United States Patent [19]

Pearson et al.

[11] 4,108,607
[45] Aug. 22, 1978

[54] BLOOD GAS SIMULATOR

[75] Inventors: Bert David Pearson, Round Lake Beach, Ill.; Richard J. Kissane, Los Alamos, N. Mex.

[73] Assignee: Baxter Travenol Laboratories, Inc., Deerfield, Ill.

[21] Appl. No.: 653,686

[22] Filed: Jan. 30, 1976

Related U.S. Application Data

[63] Continuation-in-part of Ser. No. 615,749, Sep. 22, 1975, abandoned.

[51] Int. Cl.$^2$ .............. A61M 1/03; G01N 31/00; G01N 33/16
[52] U.S. Cl. .............. 23/253 R; 23/230 B; 23/258.5 A; 128/DIG. 3
[58] Field of Search .......... 23/253 R, 254 R, 258.5 R, 23/258.5 A, 258.5 B, 258.5 BH, 258.5 M, 258.5 MH; 73/19 R; 128/DIG. 3; 261/DIG. 28; 55/159, 196, 178

[56] References Cited

U.S. PATENT DOCUMENTS

| | | | |
|---|---|---|---|
| 3,118,736 | 1/1964 | Taylor | 23/253 R X |
| 3,482,575 | 12/1969 | Claff et al. | 23/258.5 MH |
| 3,729,377 | 4/1973 | Leonard | 23/258.5 B |
| 3,779,708 | 12/1973 | Runck et al. | 23/253 R X |
| 3,827,860 | 8/1974 | Burlis | 23/258.5 B |
| 3,832,139 | 8/1974 | Runck et al. | 23/254 R X |
| 3,854,876 | 12/1974 | Rankine et al. | 23/253 R X |
| 3,892,534 | 7/1975 | Leonard | 23/258.5 B |
| 3,920,396 | 11/1975 | Schuy | 23/254 R X |

OTHER PUBLICATIONS

A Disposable Polyethylene Oxygenator System–Rygg et al.—Act Chirurgica Scandinaviia, vol. 112#6, May 25, 1957.
Journal of Thoracic and Cardiovascular Surgery–vol. 53, #4; Apr., 1967, Rotating Membrane Oxygenator.

*Primary Examiner*—Morris O. Wolk
*Assistant Examiner*—Michael S. Marcus
*Attorney, Agent, or Firm*—Paul C. Flattery; Gerald S. Geren

[57] ABSTRACT

A test system for testing the efficiency of blood oxygenators. The system includes a deoxygenator having a mixing section, a defoaming section and a collection section. Blood and deoxygenating gas are supplied to the mixing section. Mixed blood and gas exiting the mixing section enters the defoaming section where the mixture is defoamed. A portion of the deoxygenated and defoamed blood is directed to the oxygenator under test and the remainder is directed to an overflow reservoir. Blood exiting both the oxygenator and the reservoir is recirculated to the mixing section of the deoxygenator. Test sites are provided immediately upstream and downstream of the oxygenator under test so that the condition of the blood can be checked at both points and the efficiency of the oxygenator determined.

The system provides for the precise control of the condition of the blood exiting the deoxygenator.

7 Claims, 1 Drawing Figure

BLOOD GAS SIMULATOR

CROSS-REFERENCE TO RELATED APPLICATION

This application is a continuation-in-part of U.S. patent application Ser. No. 615,749 filed Sept. 22, 1975, now abandoned.

BACKGROUND OF THE INVENTION

This invention relates to a blood oxygenator test device, and more particularly, to a simulator for testing the efficiency of such oxygenators.

Blood oxygenators are devices used during cardiopulmonary or heart-lung bypass surgery to oxygenate blood received from a patient. Membrane oxygenators of the type sold by Travenol Laboratories, Inc., under Catalog No. 5M0316 are representative of such oxygenators.

In order to select an oxygenator for use under varying surgical conditions, it is important to know the efficiency and operating characteristics of the oxygenator. Fundamentally, blood oxygenators are gas transfer devices in which carbon dioxide ($CO_2$) is removed from "deoxygenated" or venous blood and is replaced by oxygen ($O_2$) to provide "oxygenated" or arterial blood. In order to accurately evaluate the gas transfer efficiency of an oxygenator, it is necessary to provide a test device which supplies carefully conditioned blood to the oxygenator under test. The blood conditions which are carefully controlled are saturation, pH, oxygen pressure ($pO_2$) and carbon dioxide pressure ($pCO_2$).

Oxygenators are presently tested by placing a live animal on a heart-lung bypass to provide a living "deoxygenator" which supplies venous blood to the oxygenator under test. The range of test conditions possible with experiments using live animals is limited by the metabolic rate of an anesthesized animal and the narrow limits over which inspired gases can be varied. These limitations on the range of test conditions prevents meaningful testing of oxygenators under carefully controlled conditions.

It is therefore an object of this invention to provide an oxygenator test apparatus which permits the testing of oxygenators over a wide range of test conditions.

These and other objects of this invention will become apparent from the following description and appended claims.

SUMMARY OF THE INVENTION

There is provided by virtue of this invention an oxygenator test apparatus which permits the testing of oxygenators over a wide range of carefully controllable test conditions. The test device includes a variable capacity deoxygenator for continuously deoxygenating a quantity of blood. The deoxygenator includes mixing, defoaming and collection sections. A blood inlet and a deoxygenating gas inlet are provided in the mixing section, and the blood and deoxygenating gas mix in the mixing section and then pass to a defoaming section. From the defoaming section, the deoxygenated blood passes to a collection point where it is directed to the oxygenator and to an overflow reservoir. Blood from the deoxygenator is delivered into the oxygenator under test in relation to the capacity of the oxygenator and any excess blood flows to the overflow reservoir. Oxygenated blood exiting the oxygenator is directed back to the blood inlet and deoxygenated blood from the reservoir is also directed back to the blood inlet.

The deoxygenator volume or size can be varied in relation to the size of the oxygenator so as to efficiently provide a sufficient quantity of deoxygenated blood to the oxygenator under test.

The deoxygenating gases are a mixture of nitrogen ($N_2$), oxygen ($O_2$) and carbon dioxide ($CO_2$) which are mixed under controlled conditions before mixing with the blood in order to provide deoxygenated blood having controllable pH, $pO_2$, $pCO_2$ and saturation.

BRIEF DESCRIPTION OF THE DRAWING

The drawing is a diagrammatic representation of the test system.

DESCRIPTION OF THE PREFERRED EMBODIMENT

Figure 1:
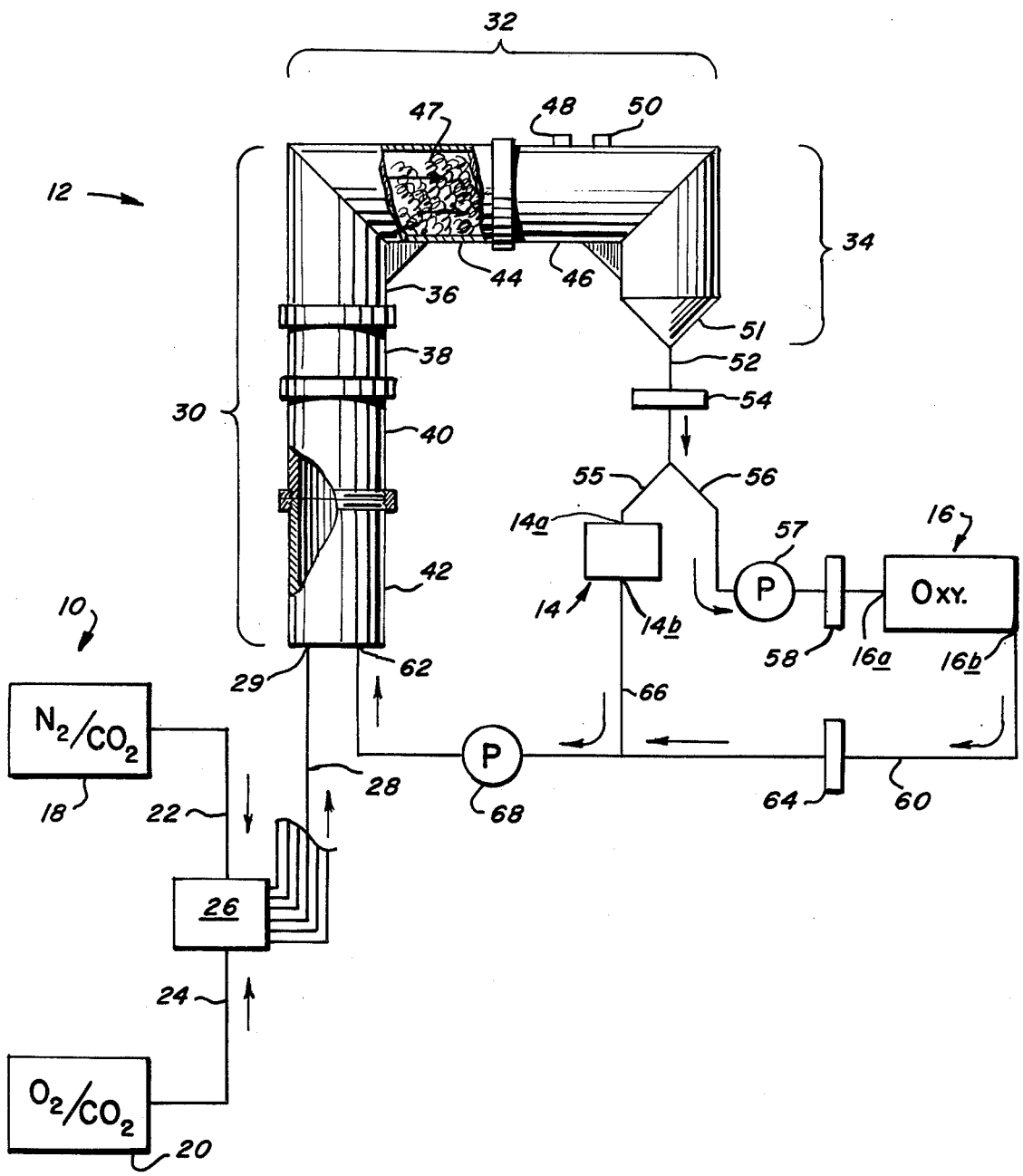

Referring now to the drawing, the test system includes a source for deoxygenating gas 10, a deoxygenator 12, an overflow reservoir 14 and the test oxygenator 16.

Deoxygenating Gas

The deoxygenating gases used in this system are $N_2$, $CO_2$ and $O_2$. In the test system disclosed herein, tanks 18 and 20 of pressurized gases are provided. The tank 18 contains 92% $N_2$ by volume and 8% $CO_2$ by volume. The tank 20 contains 95% $O_2$ and 5% $CO_2$. The gases in these tanks flow through lines 22 and 24 to two flow meters shown as 26 where the gases are mixed and their flow rates are regulated. From the flow meters 26, the gases flow through six separate lines, such as 28, to six separate inlets, such as 29. Each inlet is a sparger (not shown) located at the bottom of the deoxygenator 12.

In another arrangement three gas sources are used: one for $N_2$; one for $CO_2$; and one for $O_2/CO_2$ as in tank 20. Although three separate sources are used, the mixing and sparger systems are substantially identical.

The Deoxygenator

The deoxygenator 12 has an inverted L-like shape and includes a hollow mixing section 30, a hollow defoaming section 32 and a hollow short collection section 34.

The mixing section 30 is substantially vertically oriented and includes one leg 36 of an elbow assembly 36–44 and three separate tubular sections 38, 40 and 42. The three lower sections 38, 40 and 42 are of different lengths and can be removed individually or in combination so as to adjust the height and thereby the volume of the mixing section. The length and volume of the mixing section are important because the blood and deoxygenating gas must be in contact with each other for a sufficient length of time to permit the gas transfer to equilibrate so as to provide deoxygenated blood having the desired conditions.

The length of time in which the gas and blood are in contact is known as residence time. The residence time can be controlled by the height and volume of the mixing section, as well as by the gas and blood flow rate into the mixing section. Furthermore, the quantity of blood in the deoxygenator can be matched to the capacity of the oxygenator by varying the volume of the mixing section. Thus a large quantity of blood need not be used to test a small capacity oxygenator.

In the particular device, the tubular sections 36, 38, 40 and 42 are large diameter transparent plastic sections which are connected together by collars. The height of the column is approximately 5 feet, and its inner diameter is approximately 3¾ inches.

The defoaming section 32 is connected to the top of the mixing section and is substantially horizontally oriented. This section is made of two sections of transparent plastic conduit 44 and 46 which are connected by a collar. The sections 44 and 46 are each a leg of the elbow assemblies 36–44 and 46–51, respectively. Silicone sponge defoamers 47 are removably positioned in the defoaming section so that the mixed blood and gas from the mixing section must pass through the defoamers in order to remove entrained gas. Vents 48 and 50 are provided for venting any gas removed by the defoamers and for the addition of chemicals to the blood.

The collection section 34 is vertically oriented and is positioned at the outlet end of the defoaming section. This section has a funnel-shaped lower end and is made of a single length of transparent plastic conduit 51, which is also a leg of the elbow assembly 46–51. Deoxygenated and defoamed blood collects in the section 34 and is directed from there via line 52 to a test site or sampling area 54 for determining the condition of the blood exiting the deoxygenator. Downstream of the test site the line 52 branches into lines 55 and 56 for flow to the reservoir and oxygenator.

The Overflow Reservoir and The Oxygenator

Blood from the deoxygenator is directed to the oxygenator 16 through line 56 and to the overflow reservoir 14 through line 55. The deoxygenator produces deoxygenated blood in excess of the oxygenator's capacity so as to assure an adequate supply of blood for the oxygenator.

A pump 57 is positioned in line 56 upstream of the oxygenator so as to control the blood flow rate through the oxygenator. A test site or sampling station 58 is also placed upstream of the oxygenator so as to permit a determination of the condition of the blood entering the oxygenator. Deoxygenated blood enters the oxygenator inlet 16a and oxygenated blood exits through the outlet 16b. The return line 60 is connected to the outlet 16b and to an inlet 62 in the mixing section 30. Thus the oxygenated blood is recirculated to the mixing section 30 for reuse so as to provide a continuous or recirculating system. A test site or sampling station 64 can be positioned downstream of the oxygenator so as to provide for the determination of the blood condition at that point.

The reservoir 14 is an overflow reservoir for receiving blood produced by the deoxygenator in excess of the oxygenator's capacity. This excess blood enters the reservoir through inlet 14a and exits through outlet 14b which is connected to a return line 66 that connects to the oxygenator return line 60.

A second pump 68 is positioned downstream of the junction of the two return lines and its speed is slightly higher than that of the upstream pump so as to prevent the oxygenator from being pumped dry.

A comparison of the test results of the upstream and downstream test sites 58 and 64 provides the necessary data to determine efficiency of the oxygenator.

EXAMPLE

In a specific example, in order to test a 2.25 square meter membrane oxygenator, the deoxygenating column 10 is filled with 10 liters of fresh heparinized canine blood. The gas flow rate of $N_2/CO_2$ from the tank 18 is adjusted to approximately 30 liters per minute (l/m) and the gas flow rate of $O_2/CO_2$ from the tank 20 is adjusted to approximately 2 l/m. Thus the total flow rate of deoxygenating gas entering the bottom of the mixing section is approximately 32 l/m. In the mixing section, the gas and blood mix and move upwardly in the section under the buoyant effect of the gas. By the time they reach the defoaming section, the gas and blood are sufficiently mixed.

The deoxygenated blood then is defoamed and collected for distribution. With this arrangement, approximately 8 l/m of blood exits the collection section 34. The oxygenator's flow rate capacity is about 6 l/m so that about 2 l/m flow into the overflow reservoir.

Once the system has been equilibrated, blood samples are taken at the upstream test site 58 and downstream test site 64 and analyzed for pH, $pO_2$, $pCO_2$ and saturation. A comparison of these test results permits a determination of the efficiency of the oxygenator 16.

With reference to the deoxygenator, in one test the blood conditions entering the deoxygenator were: saturation 84%, pH 7.43, $pCO_2$ 43 mm Hg and $pO_2$ 51 mm Hg; while blood exiting the deoxygenator had the following conditions: saturation 60%, pH 7.40, $pCO_2$ 47 mm Hg and $pO_2$ 33 mm Hg.

Other sized oxygenators can be tested. For example, there is available 1.1 square meter pediatric membrane oxygenator that can be tested. In that event, the column size as shown herein could be used but the excess capacity would be unreasonably great. Thus one of the sections is removed so that the volume of blood necessary and capacity of the deoxygenator is reduced. After the sections are removed, the system is adjusted as described before in order to equilibrate the system and then the efficiency of the oxygenator is tested.

It will be appreciated that ratios of $N_2/CO_2/O_2$ can be varied so as to obtain different deoxygenating conditions. Furthermore, the gas flow rates, as well as the column volume, can also be varied so as to provide control over the pH, $pO_2$, $pCO_2$ and saturation of blood entering the oxygenator. This type of a control permits testing of the oxygenator under a wide variety of test conditions.

It will be appreciated that numerous changes and modifications can be made to the embodiment shown herein without departing from the spirit and scope of this invention.

What is claimed is:

1. A system for use in evaluating the efficiency of a blood oxygenator, comprising:
    (a) a deoxygenator means for deoxygenating a quantity of blood having a blood inlet, a deoxygenating gas inlet and a deoxygenating blood outlet;
    (b) said deoxygenator including
       (1) a hollow substantially upright mixing section having said blood inlet and said deoxygenating gas inlet in the lower portion of said section;
       (2) a hollow substantially transversely oriented defoaming section connected with said mixing section for receiving blood which has been mixed with said gas and wherein said mixture is defoamed; and
       (3) a hollow collection section connected with said defoaming section for receiving defoamed blood from said defoaming section, said collection means including outlet means through which deoxygenated blood exits said deoxygenator;

(c) a source for deoxygenating gas to be mixed with said blood which is connected with said gas inlet;

(d) a blood oxygenator means having an inlet and an outlet, with said inlet being connected with the outlet of the deoxygenator means so that deoxygenated blood is directed into said oxygenator means, and with said oxygenator means outlet being connected with said deoxygenator means blood inlet for directing oxygenated blood to said deoxygenator means;

(e) sampling and testing means communicating with said oxygenator means for obtaining and testing samples of the blood entering said oxygenator means and exiting said oxygenator means for determining the efficiency of a blood oxygenator;

(f) an overflow reservoir connected with said deoxygenator blood outlet for receiving from said deoxygenator, blood in excess of the capacity of the oxygenator means; and (g) conduit means connected with said reservoir and deoxygenator means for returning said excess blood to said deoxygenator means.

2. A system as in claim 1, which further includes means for selectively controlling the volume of the deoxygenator means.

3. A deoxygenator as in claim 1, wherein said mixing section includes a plurality of removable hollow tubular sections for selectively adjusting the length of the column.

4. A deoxygenator as in claim 3, wherein said sections are of different lengths.

5. A deoxygenator as in claim 1, wherein said column is of a length sufficient to assure effective mixing of said blood and deoxygenating gas.

6. A deoxygenator as in claim 1, which further includes defoaming means positioned within said defoaming section.

7. A deoxygenator as in claim 1, wherein said deoxygenator has an inverted L-shape with the mixing section forming the long leg and the defoaming section forming the short leg.

* * * * *